Figure 1:
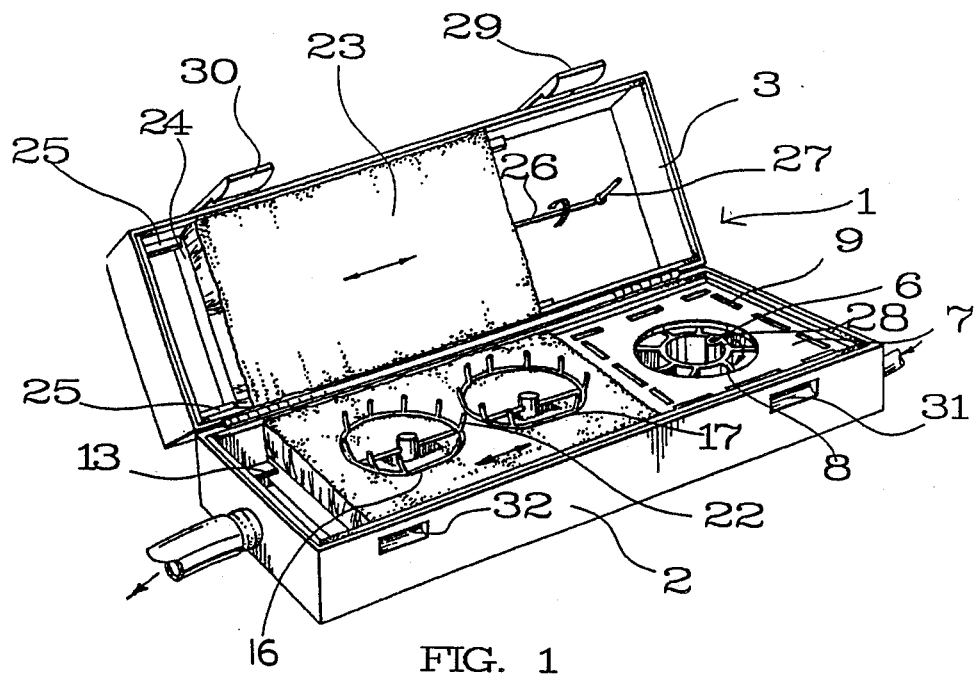

United States Patent [19]

Pinsonneault

[11] Patent Number: 4,891,857
[45] Date of Patent: Jan. 9, 1990

[54] DENTURE CLEANING DEVICE

[76] Inventor: Otto Pinsonneault, P.O. Box 1959, Vernon, Canada, V1T 8Z7

[21] Appl. No.: 216,375

[22] Filed: Jul. 8, 1988

[30] Foreign Application Priority Data

Oct. 2, 1985 [CA] Canada ................................. 492041

[51] Int. Cl.4 ............................................. A46B 13/06
[52] U.S. Cl. .................................... 15/21 R; 15/97 R
[58] Field of Search ................. 15/21 R, 21 B, 33, 39, 15/74, 97 R

[56] References Cited

U.S. PATENT DOCUMENTS

| | | | |
|---|---|---|---|
| 2,301,931 | 11/1942 | Davis | 15/21 R X |
| 3,066,336 | 12/1962 | Stobbe | 15/21 R |
| 3,774,256 | 11/1973 | Gauthier | 15/21 R |

Primary Examiner—Edward L. Roberts
Attorney, Agent, or Firm—Larson and Taylor

[57] ABSTRACT

A denture cleaning apparatus comprising a housing having a water inlet and a water outlet, a turbine wheel adapted to be driven by water flowing through the housing, a pair of opposed brush members slidably mounted in the housing, a mechanism for receiving dentures between the brush members, and a mechanism driven by the turbine wheel for reciprocating the brush members so as to clean dentures located therebetween.

8 Claims, 1 Drawing Sheet

DENTURE CLEANING DEVICE

This invention relates to an apparatus for cleaning dentures.

People who wear dentures continually face the problem of adequate cleaning. For reasons of hygiene, all food particles and bacteria must be removed. Hitherto, apart from manual brushing which is unsatisfactory, dentures have been cleaned by leaving them to soak in cleaning solution. However, this method requires them to be left for sometime and is relatively inefficient.

An object of the invention is to provide a denture cleaning apparatus that can alleviate the aforementioned problems.

According to the present invention there is provided a denture cleaning apparatus comprising a housing having a water inlet and a water outlet, a turbine wheel adapted to be driven by water flowing through the housing, a pair of opposed brush members or brushes mounted in the housing, means for receiving dentures between the brush members, and means driven by the turbine wheel for providing reciprocal relative motion between the brush members and the dentures and in particular for slidably reciprocating the brush members so as to clean dentures located therebetween.

Such an apparatus cleans the dentures mechanically owing to the reciprocating motion of the brushes driven by the turbine, which brushes are turned by the action of water flowing through the housing. The apparatus can be made portable and conveniently connected to domestic water outlets. Provision can be made for the addition of a cleanser to the housing.

In a preferred embodiment the housing is in the form of a box with a hinged lid, one of the brushes being mounted in the lid and the other in the body of the housing so that when the lid is closed the brushes are brought into opposed relationship with the dentures located between them. The box is conveniently a rectangular plastic box with snap-fitting closures for the lid.

Figure 2:
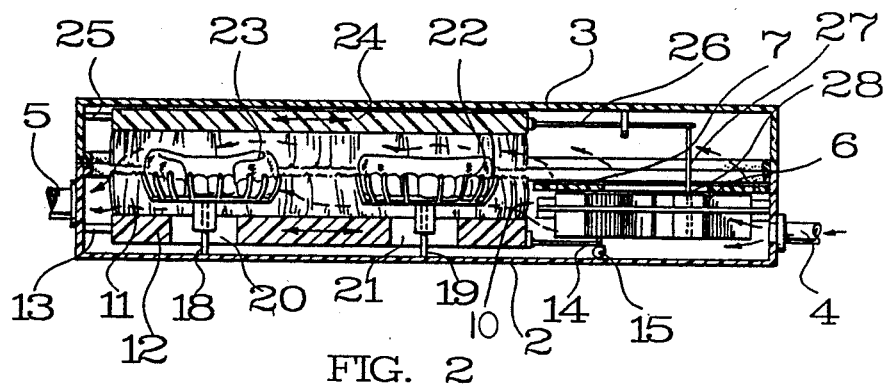

The invention will now be described in more detail, by way of example only, with reference to the accompanying drawings, in which:

FIG. 1 is a perspective view of a denture cleaning apparatus with the lid open; and FIG. 2 is a cross-sectional view of the apparatus shown in FIG. 1.

In the drawings, the denture cleaning apparatus comprises a housing 1 in the form of a rectangular box with a bottom 2 and a hinged recessed lid 3. The bottom 2 has a water inlet 4 and water outlet 5 fitted with plastic hoses for connection respectively to a domestic water outlet and drain hole.

A turbine wheel 6 adjacent the inlet 4 is rotatably mounted in a turbine chamber between slotted plate 7 and the floor of the housing 1. The inlet 4 is offset relative to the rotational axis of the turbine wheel 6 and water impinging on curved turbine blades 8 of turbine wheel 6 drive the turbine wheel 6 in rotation. After impinging on the turbine blades 8, the water flows into the main part of the housing 1 through slots 9 in the plate 7 and also through open side 10 of the turbine chamber.

A brush 11 with a base plate 12 is slidably fitted on tracks 13 in the bottom 2 of the housing. The brush 11 is eccentrically coupled to the turbine wheel 6 by link arm 14 and crank pin 15 so that rotation of the turbine wheel 6 causes the brush 11 to undergo a reciprocating motion on tracks 13 in the bottom of the housing. The link arm 14 is connected to the base plate 12 of the brush 11 by a swivel mounting.

A pair of open cage-like denture holders 16,17 are fixed to the floor of the housing 1 by pedestals 18,19 extending through slots 20,21 in the base plate 12 of the brush 11. The holders have resilient curved upstanding pins 22 that loosely support the dentures 23 placed in the central recesses of the denture holders.

A second brush 23 with a base plate 24 is slidably mounted on tracks 25 in the recessed lid 3 of the housing. When the lid is closed, the brush 23 is eccentrically coupled to the turbine wheel 6 by link arm 26 and crank pin 27 that fits into hole 28 in the turbine wheel. The link arm 26 is connected to the base plate 24 of the brush 23 by a swivel mounting. The second brush 23 is driven in reciprocation by the turbine wheel 6 in the opposite direction to the brush 11 the crank pins 15,27 are being coupled to the wheel at diametrically opposed locations.

A pair of snap closure members 29,30 on the lid 3 fit into corresponding recesses 31,32 in the first wall of the bottom 2 of the housing.

The cleaning apparatus can be made compact and portable. To use it, the owner merely has to connect the inlet hose to a domestic water outlet, place the drain hose in a sink, and locate the denture in the denture holder 16,17. He then snaps the lid closed, after optionally adding cleansing fluid, and turns on the tap. Water flowing through the housing 1 drives the turbine wheel 6, which reciprocates the brushes in opposite directions. The water then flows out of the outlet 5 after bathing the brushes 11,23.

The dentures are loosely fitted in the denture holders 16,17 and turn round with the reciprocating movement of the brushes so that they are thoroughly cleansed all over. After about 30 seconds, the tap can be turned off, the water remaining in the housing drained into the sink, and the dentures removed sparkling clean.

The cleaning apparatus can be in the form of a double unit, as shown, or a single unit, which can be made smaller to fit in a shaving kit or cosmetic bag. With the exception of the brushes, the entire unit is made of plastic. The brushes are constructed of a plastic backing plate and tooth brush style bristles.

I claim:

1. A denture cleaning apparatus comprising a housing having a water inlet and a water outlet, a turbine wheel adapted to be driven by water flowing through the housing, a pair of opposed brush members slidably mounted in the housing, means for receiving dentures between the brush members, and means driven by the turbine wheel for reciprocating the brush members so as to clean dentures located therebetween.

2. An apparatus according to claim 1, wherein said housing comprises a box with a hinged lid, one of said brush members being mounted in the lid so that it is brought down into opposed relationship with the other brush member when the lid is closed.

3. An apparatus according to claim 2, wherein said brush members are located in the path of water flowing through said housing.

4. An apparatus according to claim 3, wherein each said brush member is coupled to said turbine wheel by a link arm and crank pin disposed so that the brush members are driven in opposite directions.

5. An apparatus according to claim 4, wherein said box is a rectangular plastic box, said inlet being provided with a hose for connection to a domestic water outlet.

6. An apparatus according to claim 1, wherein said denture receiving means comprises an open cage fixed to the housing, the denture fitting loosely into said open cage.

7. An apparatus according to claim 4, wherein said cage is mounted on a pedestal extending through a slot in a base of one of said brush members to permit reciprocating movement of said one brush member relative to said open cage.

8. A denture cleaning apparatus comprising a housing having a water inlet and a water outlet, a turbine wheel adapted to be driven by water flowing through the housing, a pair of opposed brush members mounted in the housing, means for receiving dentures between the brush members, and means driven by the turbine wheel for providing reciprocating relative motion between the brush members and dentures located in said denture receiving means so as to clean the dentures.

* * * * *